(12) United States Patent
Watts et al.

(10) Patent No.: US 9,452,223 B2
(45) Date of Patent: Sep. 27, 2016

(54) MATERIALS AND METHODS RELATING TO GLYCOSYLATION

(75) Inventors: Andrew Graham Watts, Bath (GB); Amanda Barbara MacKenzie, Bath (GB); Terrence Kantner, Bath (GB)

(73) Assignee: Glythera Limited, Newcastle Upon Tyne (GB)

(*) Notice: Subject to any disclaimer, the term of this patent is extended or adjusted under 35 U.S.C. 154(b) by 643 days.

(21) Appl. No.: 13/378,192

(22) PCT Filed: Jun. 16, 2010

(86) PCT No.: PCT/GB2010/001188
§ 371 (c)(1),
(2), (4) Date: Mar. 7, 2012

(87) PCT Pub. No.: WO2010/146362
PCT Pub. Date: Dec. 23, 2010

(65) Prior Publication Data
US 2012/0190631 A1 Jul. 26, 2012

Related U.S. Application Data

(60) Provisional application No. 61/187,434, filed on Jun. 16, 2009.

(51) Int. Cl.
| | | |
|---|---|---|
| C07H 5/06 | (2006.01) |
| C07K 14/47 | (2006.01) |
| C07K 14/555 | (2006.01) |
| C07K 14/54 | (2006.01) |
| C07K 14/52 | (2006.01) |
| A61K 31/7008 | (2006.01) |
| C07K 14/62 | (2006.01) |
| C07K 14/61 | (2006.01) |
| C07K 1/107 | (2006.01) |
| C07K 14/53 | (2006.01) |
| C12P 19/26 | (2006.01) |
| C07K 16/00 | (2006.01) |
| A61K 47/48 | (2006.01) |

(52) U.S. Cl.
CPC ..... *A61K 47/4823* (2013.01); *A61K 47/48092* (2013.01)

(58) Field of Classification Search
CPC ........ C07H 15/22; A61K 38/02; C07K 2/00; C07K 17/10
USPC ............. 536/17.8; 530/322, 395, 351, 391.1, 530/399, 381
See application file for complete search history.

(56) References Cited

U.S. PATENT DOCUMENTS

| | | |
|---|---|---|
| 5,770,407 A | 6/1998 | Wong et al. |
| 6,927,042 B2 * | 8/2005 | Schultz et al. ............... 435/69.1 |
| 7,226,903 B2 | 6/2007 | DeFrees et al. |

FOREIGN PATENT DOCUMENTS

| | | |
|---|---|---|
| WO | 92/16640 | 10/1992 |
| WO | 03/031464 A2 | 4/2003 |
| WO | 2008/124406 A2 | 10/2008 |
| WO | 2009/062100 A1 | 5/2009 |

OTHER PUBLICATIONS

"Cytidine monophosphate", SciFinder results; obtained Apr. 1, 2014.*
"Cytosine monophosphate", SciFinder results; obtained Apr. 1, 2014.*
Watts, A. G. et al., Journal of the American Chemical Society, "Trypanosoma cruzi Trans-sialidase Operates through a Covalent Sialyl-Enzyme Intermediate: Tyrosine is the Catalytic Nucleophile", 2003, vol. 125, pp. 7532-7533.*
Zeng, X. et al., Carbohydrate Research, "Convenient enzymatic synthesis of a p-nitrophenyl oligosaccharide series of sialyl N-acetyllactosamine, sialyl Lex and relevant compounds", 2005, vol. 340, pp. 2469-2475.*
Alakomi, H.-L. et al., Applied and Environmental Microbiology, "Lactic Acid Permeabilizes Gram-Negative Bacteria by Disrupting the Outer Membrane", May 2000, vol. 66, No. 5, pp. 2001-2005.*
Amaya, M. F. et al., Structure, "Structural Insights into the Catalytic Mechanism of Trypanosoma cruzi trans-Sialidase", May 2004, vol. 12, pp. 775-784.*
Boons, G.-J. et al., Chemical Reviews, "Recent Advances in O-Sialylation", 2000, vol. 100, pp. 4539-4565.*
Martini, M. C. et al., The American Journal of Clinical Nutrition, "Strains and species of lactic acid bacteria in fermented milks (yogurts): effect on in vivo lactose digestion", 1991, vol. 54, pp. 1041-1046.*
Mitchell, F. L. et al., Biochemistry, "Insights into the Activity and Specificity of Trypanosoma cruzi trans-Sialidase from Molecular Dynamics Simulations", 2013, vol. 52, pp. 3740-3751.*
Bucchini, Sabrina et al., "A New Generation of Specific Trypanosoma cruzi trans-Sialidase Inhibitors", Angew. Chem. Int. Ed., 47: 2700-2703 (2008).
Newstead, Simon L. et al., "The Structure of Clostridium perfringens Nani Sialidase and its Catalytic Intermediates", J. Biol. Chem., 283(14): 9080-9088 (2008).
Parker, Laura L. et al., "Rationalization of the Differences in Lifetime of Two Covalent Sialosyl-Enzyme Intermediates of Trypanosoma rangeli Sialidase", J. Phys. Chem., 112(45): 14093-14095 (2008).

(Continued)

*Primary Examiner* — Shaojia Anna Jiang
*Assistant Examiner* — Bahar Craigo
(74) *Attorney, Agent, or Firm* — Patrick J. Hagan; Dann, Dorfman, Herrell and Skillman, P.C.

(57) ABSTRACT

Techniques to glycosylation are described, and more particularly to the production of glycosylation structures that are resistant to enzymatic degradation, thereby modulating one or more of their biological properties or those of therapeutic moieties incorporating them, and in particular to reacting activated carbohydrate substrates containing fluorine, such as 3-fluoro sialic acid compounds, with sugar acceptors to produce covalent conjugates of the sugar acceptor and one or more of the sialic acid compounds.

38 Claims, No Drawings

(56) References Cited

OTHER PUBLICATIONS

Sun, Xue-Long et al., "Syntheses of C-3-Modified Sialylglycosides as Selective Inhibitors of Influenza Hemagglutinin and Neuraminidase", Eur. J. Org. Chem., 2643-2653 (2000).
Notice of Reasons for Rejection, dated Aug. 1, 2014, issued in corresponding Japanese Patent Application No. 2012-515554.
Decision of Rejection, dated Feb. 9, 2015, issued in corresponding Japanese Patent Application No. 2012-515554.
Chokhawala, Harshal A. et al., "Enzymatic Synthesis of Fluorinated Mechanistic Probes for Sialidases and Sialytransferases", J. Am. Chem. Soc., 129: 10630-10631 (2007).
Watts, Andrew G. et al., "The synthesis of some mechanistic probes for sialic acid processing enzymes and the labeling of a sialidase frmo Trypanosoma rangeli", Can. J. Chem., 82: 1581-1588 (2004).
Burkart, Michael D. et al., "An efficient synthesis of CMP-3-fluoroneuraminic acid", Chem. Commun., 16: 1525-1526 (1991).
Hagiwara et al., "Inhibition of bacterial and viral sialidases by 3-fluoro-N-acetylneuraminic acid", Carbohydrate Research, 263: 167-172 (1994).

\* cited by examiner

MATERIALS AND METHODS RELATING TO GLYCOSYLATION

CROSS-REFERENCE TO RELATED APPLICATIONS

This application is the U.S. National Stage of International Application No. PCT/GB2010/001188, filed Jun. 16, 2010, which claims priority from U.S. Provisional Application No. 61/187,434, filed Jun. 16, 2009. The entire disclosure of the aforesaid application is incorporated by reference in the present application.

FIELD OF THE INVENTION

The present invention relates to materials and methods relating to glycosylation, and more particularly to the production of glycosylation structures that are resistant to enzymatic degradation, thereby modulating one or more of their biological properties or those of therapeutic moieties incorporating them. More specifically, the present invention involves reacting activated carbohydrate substrates containing fluorine, such as 3-fluoro sialic acid compounds, with sugar acceptors to produce covalent conjugates of the sugar acceptor and one or more of the sialic acid compounds.

BACKGROUND OF THE INVENTION

Most naturally occurring polypeptides contain carbohydrate moieties covalently attached to the polypeptide at some of the amino acids residues of the primary polypeptide chain. These polypeptides are generally referred to in the art as glycopeptides or glycoproteins. It is also known that the nature of the glycosylation pattern on any given polypeptide can affect its properties, including protease resistance, intracellular trafficking, secretion, tissue targeting, biological half life and antigenicity when the polypeptide is present in a biological system such as a cell or individual.

The glycosylation of polypeptides is a natural form of post-translational modification that alters the structure and function of polypeptides. In nature, glycosylation is introduced by enzymatic processes that lead to site specific modification of different types of glycosylated polypeptides. In N-linked glycosylation, glycans are attached to the amide nitrogen of asparagine side chains and in O-linked glycosylation, glycans are attached to the hydroxy oxygen of serine and threonine side chains. Other forms of glycosylation include glycosaminoglycans which are attached to the hydroxy oxygen of serine, glycolipids in which the glycans are attached to ceramide, hyaluronan which is unattached to either protein or lipid, and GPI anchors which link proteins to lipids through glycan linkages.

There is a general problem in the art in that glycosylation is often added to polypeptides in eukaryotic cells, but is rarely added to polypeptides expressed in the prokaryotic hosts often used for the recombinant expression of therapeutic polypeptides. This absence of glycosylation in polypeptides produced in prokaryotic hosts can lead to the polypeptides being recognised as foreign or mean that they have the properties that otherwise differ from their native forms. There is also a problem that it is difficult to engineer glycosylation into polypeptides at sites where there is not native glycosylation, in an attempt to use this to modulate the properties of the polypeptides.

There have therefore been attempts in the art to introduce or modify the glycosylation pattern of polypeptides, for example in situations where the expression of the polypeptide might cause a change to the natural glycosylation pattern of the polypeptide (e.g. expression in bacterial hosts) or where it is desired to modify the glycosylation pattern of the polypeptide in the hope of improving one or more of the characteristics of the polypeptide, especially where the polypeptide is a therapeutic protein. For example, see the modification of interferon beta described in U.S. Pat. No. 7,226,903.

The glycan molecules that are attached to polypeptides have a range of linear and branched structures and different lengths of glycan chain and the specific glycan molecules present on a polypeptide affects the characteristics of the polypeptide. Many types of glycan molecules include terminal sialic acids. These nine-carbon sugars, which bear a negative charge at physiological pH, are known to be involved in ligand-receptor interactions that can greatly affect specific cell-cell, pathogen-cell, or drug-cell communications. One particular characteristic of glycan chains that include terminal sialic acid residues is that they increase the half life of therapeutic polypeptides glycosylated with them. This is known from the observation that polypeptides comprising glycans without terminal sialic acid residues are rapidly removed from the circulation by the liver, thereby reducing the half-life of the therapeutic polypeptide.

Fluorine substituted sugars have been used as non processible substrates for use in crystallising enzymes such as CstII (Chiu et al., Nat. Struct. Mol. Biol. (2004) 11, 163-170). In this context, the fluorine containing saccharides are known to be resistant to enzymatic processing where the glycosyl transferase is acting upon the glycosidic linkage of the fluorine containing carbohydrate.

A 2,3-difluorosialic acid derivative has been synthesized and used as an inactivator of sialidases from the parasites *Trypanosoma cruzi* (Watts et al., J. Am. Chem. Soc. (2003) 125, 7532-7533) and *Trypanosoma rangeli*. (Watts et al., Can. J. Chem. (2004) 82, 1581-1588). This initial work led to the discovery that these sialidases operate through the involvement of a covalent sialosyl-enzyme intermediate and established that compounds such as this derivative acted as time-dependant covalent inactivators of Trypanosomal sialidases.

Subsequently, it has also been shown that a 2,3-difluoro neuraminic acid derivative which has a hydroxyl group at C-5 rather than the natural N-acetyl group also acts as a covalent inactivator of *T. rangeli* sialidase, but displays very different kinetic behaviour ($k_{inact}$ and $k_{react}$) to the original inhibitor (Watts et al., J. Biol. Chem. (2006) 281, 4149-4155).

In summary, the modification of the glycosylation of polypeptides, especially to modify their biological properties, remains a challenging problem and one that has not been addressed in a satisfactory manner in the prior art.

SUMMARY OF THE INVENTION

Broadly, the present invention is based on the recognition that fluoro sialic acid compounds, such as 3-fluoro sialic acid compounds, can be used to form conjugates with sugar acceptors that modulate one or more of the biological properties of the conjugate or of a therapeutic moiety that incorporates the conjugate. Thus, modified glycosylation structures produced using these methods may be introduced into or be a part of therapeutic moieties, such as polypeptide. Thus, in one aspect, the present invention relates to methods for reacting an activated 3-fluoro sialic acid compound with a sugar acceptor group, where the 3-fluoro sialic acid compound is not attached to a CMP group, as conventionally used in the prior art. The methods may be carried out enzymatically, e.g. using a sialyl transferase, a trans-sialidase or using synthetic techniques from the field of sugar chemistry.

Sialyl transferases have been used to transfer sialic acid derivatives to acceptor sugars, using donors that are natural-, or modified natural-substrates for the enzymes (i.e., CMP-sialic acids or derivatives thereof). The inverting sialyl transferase PmST1 has been shown to transfer 3-fluoro-CMP sialic acid to a galactosyl acceptor, however this reaction used a two-enzyme one-pot method to generate the 3-fluoro analogue of the natural donor sugar, in situ (Harshal et al., J. Am. Chem. Soc. (2007) 129, 10630-10631. However, unnatural activated 3-fluoro sialic acids have never been transferred to a sugar acceptor using a sialyl transferase, and it has not been proposed before now to incorporate the properties of 3-fluoro sialic acids into the glycosylation structures of polypeptides.

Accordingly, in a first aspect, the present invention provides a method which comprises forming a covalent conjugate between a sugar acceptor and a 3-fluorosialic acid compound, the method comprising contacting the sugar acceptor and 3-fluoro sialic acid compound, the contacting step taking place under conditions suitable for reacting and covalently bonding the 3-fluoro sialic acid compound to the sugar acceptor, wherein the 3-fluoro sialic acid compound does not comprise a cytosine monophosphate (CMP) group.

In one embodiment, the method comprises contacting the sugar acceptor, the 3-fluoro sialic acid compound and an enzyme capable of transferring the 3-fluoro sialic acid compound to the sugar acceptor, the contacting step taking place under conditions suitable for the transfer and covalent bonding to the 3-fluoro sialic acid compound to the sugar acceptor. The enzyme may include a sialyl transferase or a trans-sialidase. Alternatively or additionally, the covalent bonding the 3-fluoro sialic acid compound to the sugar acceptor is carried out by synthetic chemical reaction.

Typically, the formation of the covalent conjugate with the 3-fluoro sialic acid compound modulates a biological property of the sugar acceptor or a therapeutic moiety comprising the sugar acceptor, for example a biological property such as resistance to enzymatic hydrolysis (e.g., by exo-sialidases or neuraminidases), biological stability or a pharmacokinetic property.

Preferably, the method is carried out as an in vitro cell-free method. Where the transfer reaction is enzymatic, it may take place with inversion at anomeric link between the 3-fluoro sialic acid compound and acceptor carbohydrate group. Unlike the prior art CMP based methods, the methods of the present invention may be carried out using one enzyme. The present invention also helps to overcome the problem that existed in the prior art that the few known examples of CMP 3-fluorosialic acid compounds have been shown to be very stable towards sialyl transferases, and are therefore not of practical use for synthesising fluoro sialic acid conjugates.

In some embodiments, the method may comprise the step of modifying glycosylation structures already present on the polypeptide, for example by virtue of the way in which it has been expressed or which have been previously synthetically made. In one typical situation, this may comprise the additional step of removing one or more terminal glycosyl groups from a glycosylation structure initially present on the polypeptide to form the acceptor group and/or replacing the terminal glycosyl group of the glycosylation structure with one or more 3-fluoro sialic acid groups. Conveniently, the step of removing the terminal glycosyl group is carried out enzymatically, for example by using a sialidase. Alternatively, an existing glycosylation structure may be subjected to further cleavage or alteration, for example removing more than a terminal glycosyl group, to provide the sugar acceptor that may be used in accordance with the present invention.

In addition, in some embodiments, the methods of the present invention may comprise transferring a plurality of 3-fluoro sialic acid groups to acceptor groups of the polypeptide. This might be done in order to provide additional protection to the core glycosylation structure to degradation. By way of example, two, three or more 3-fluoro sialic acid groups may be covalently linked to an acceptor group, either by repeating the method to link successive 3-fluoro sialic acid groups, or covalently bonding an oligomer of the 3-fluoro sialic acid groups to an acceptor. In some embodiments, the 3-fluoro sialic acid groups may be conjugated to the terminal glycosyl residue of a glycosylation structure present on the polypeptide.

Preferably, the methods disclosed in the present application employ a 3-fluoro sialic acid compound represented by general formula (I):

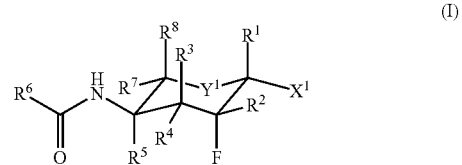

(I)

wherein:
$Y^1$ is selected from —O—, —S—, or —NR—, wherein R is independently selected from H, $C_{1-7}$ alkyl, $C_{3-10}$ heterocyclyl, or $C_{5-20}$ aryl;
$R^1$ is a good leaving group with the proviso that it is not a cytosine monophosphate (CMP) group;
$X^1$ is —$CO_2R$, wherein R is as defined above;
$R^2$ is selected from H, halide or OH;
$R^3$ and $R^4$ are each independently selected from H, —OR, —$NR_2$ or —$Z^1(CH_2)_mZ^2$, where R is as defined above, $Z^1$ is selected from —O—, —NR—, —$CR_2$— and —S—, m is from 0 to 5 and $Z^2$ is selected from —OR, —$NR_2$ or —CN; with the proviso that $R^3$ and $R^4$ cannot both be H;
$R^5$ is H;
$R^6$ is selected from $C_{1-7}$ alkyl; $C_{1-7}$ hydroxyalkyl, $C_{1-7}$ amino alkyl or $C_{1-7}$ thioalkyl;
$R^7$ is a group of formula:

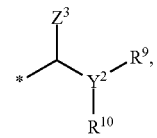

wherein $Y^2$ is selected from N, O, S, and CH; $Z^3$ is selected from H, hydroxyl, halide, $C_{1-7}$ alkyl, $C_{1-7}$ aminoalkyl, $C_{1-7}$ hydroxyalkyl, or $C_{1-7}$ thioalkyl; $R^9$ and $R^{10}$ are independently selected from H, hydroxyl, $C_{1-7}$ hydroxyalkyl, $C_{1-7}$ alkyl, $C_{5-20}$ aryl, $C(O)Z^4$, wherein $Z^4$ is selected from $C_{1-7}$ alkyl or $C_{5-20}$ aryl, with the proviso that if $Y^2$ is O or S, $R^{10}$ is absent;
or wherein $R^4$ is other than hydroxyl, $R^7$ may additionally be $C_{1-7}$ hydroxyalkyl;
$R^8$ is hydrogen;

or an oligomer of two or more molecules of formula (I); and isomers, salts, solvates, or chemically protected forms thereof.

In a further aspect, the present invention provides a conjugate of a therapeutic moiety comprising a glycosylation structure, wherein the glycosylation structure is covalently bonded to one or more 3-fluoro sialic acid groups, wherein the 3-fluoro sialic acid groups form terminal glycosyl group of the glycosylation structure. In general, the therapeutic moiety will be a polypeptide and the glycosylation structure is linked to the polypeptide at a glycosylation site and/or to one of the amino acid residues, optionally via a linker group. The use of linker groups is discussed further below.

In a further aspect, the present invention provides a glycosylation structure, wherein the glycosylation structure comprises one or more 3-fluoro sialic acid groups and wherein the 3-fluoro sialic acid groups are covalently bonded to one or more terminal glycosyl groups of the glycosylation structure. As described below, the glycosylation structure generally comprises at least one 3-fluoro sialic acid group and two further saccharide units which may be 3-fluoro sialic acid groups or a different type of saccharide unit.

In a further aspect, the present invention provides a glycosylation structure comprising one or more terminal 3-fluoro sialic groups, wherein the structure is represented by the formula:

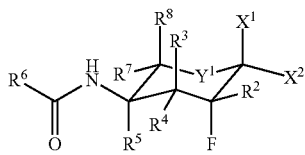

wherein:
$Y^1$ is selected from —O—, —S—, or —NR—, wherein R is independently selected from H, $C_{1-7}$ alkyl, $C_{3-10}$ heterocyclyl, or $C_{5-20}$ aryl;
$X^1$ is —$CO_2R$, wherein R is as defined above;
$X^2$ represents the remaining part of the glycosylation structure and comprises at least two saccharide units;
$R^2$ is selected from H, halide or OH;
$R^3$ and $R^4$ are each independently selected from H, —OR, —$NR_2$ or —$Z^1(CH_2)_mZ^2$, where R is as defined above, $Z^1$ is selected from —O—, —NR—, —$CR_2$— and —S—, m is from 0 to 5 and $Z^2$ is selected from —OR, —$NR_2$ or —CN; with the proviso that $R^3$ and $R^4$ cannot both be H;
$R^5$ is H;
$R^6$ is selected from $C_{1-7}$ alkyl; $C_{1-7}$ hydroxyalkyl, $C_{1-7}$ amino alkyl or $C_{1-7}$ thioalkyl;
$R^7$ is a group of formula:

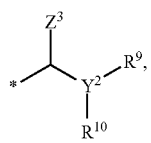

wherein $Y^2$ is selected from N, O, S, and CH; $Z^3$ is selected from H, hydroxyl, halide, $C_{1-7}$ alkyl, $C_{1-7}$ aminoalkyl, $C_{1-7}$ hydroxyalkyl, or $C_{1-7}$ thioalkyl; $R^9$ and $R^{10}$ are independently selected from H, hydroxyl, $C_{1-7}$ hydroxyalkyl, $C_{1-7}$ alkyl, $C_{5-20}$ aryl, $C(O)Z^4$, wherein $Z^4$ is selected from $C_{1-7}$ alkyl or $C_{5-20}$ aryl, with the proviso that if $Y^2$ is O or S, $R^{10}$ is absent;
or wherein $R^4$ is other than hydroxyl, $R^7$ may additionally be $C_{1-7}$ hydroxyalkyl;
$R^8$ is hydrogen;
or an oligomer of two or more molecules of formula (I); and isomers, salts, solvates, or chemically protected forms thereof.

In this formula, the $X^2$ group represents two or more saccharide units, forming a glycosylation structure or a portion thereof. The units may be one or more further 3-fluoro sialic acid groups, for example if a plurality of such groups are included in the structure, or may be any naturally occurring or modified saccharide group. As set out in more detail below, the glycosylation structure may be based on a naturally occurring or synthetic glycan and have a monoantennary structure, a biantennary structure, a triantennary structure or a complex glycosylation structure.

In a further aspect, the present invention provides a conjugate as disclosed herein for use in a method of medical treatment.

In a further aspect, the present invention provides a conjugate for use in a method of treatment as disclosed herein, wherein the treatment is therapy or diagnosis.

In a further aspect, the present invention provides the use a conjugate as disclosed herein in the preparation of a medicament for the treatment of a condition that responds to administration of the polypeptide.

In a further aspect, the present invention provides a pharmaceutical composition comprising a conjugate as disclosed herein and a pharmaceutically acceptable carrier.

Embodiments of the present invention will now be described by way of example and not limitation.

DETAILED DESCRIPTION

Fluoro Sialic Acid Compounds

As mentioned above, the present invention makes use of fluoro sialic acid compounds, and more especially 3-fluoro sialic acid compounds, to produce conjugates with useful biological properties, such as an increased resistance to enzymatic degradation. Preferred compounds useful in accordance with the present invention are represented by general formula I and/or having the substituents of the compounds disclosed in the examples in their various combinations and permutations. In general, the compounds differ from those disclosed in the prior art as they include a fluorine substituent at the 3-position to improve their resistance to enzymatic degradation and the presence of a good leaving group other than CMP at 2-position of the compound, in the case of Formula I, the $R^1$ substituent at the axial 2-position. 3-fluoro sialic acid glycosides suitable for use in accordance with the present invention can be generated chemically as exemplified in Sun et. al., Eur. J. Org. Chem. (2000), 2643-2653.

The term "leaving group" is well known and commonly used in the art, and refers to an atom or functional group which can be expelled from a molecule in a chemical reaction. As used herein, the term "leaving group" refers to a group which is labile in a nucleophilic substitution reaction. Lability/leaving group ability of a particular functional group depends on the $pK_a$ of its conjugate acid—generally speaking, the lower this is, the better the leaving group. Preferably, the leaving group is capable of supporting and stabilising a negative charge, i.e., the group is capable of leaving as an anion. Many such leaving groups are known in the art including, but not limited to, halides (F⁻, Cl⁻, Br⁻, I⁻), hydroxide (HO⁻), alkoxides (RO⁻, where R is an ether substituent as defined below), carboxylates (RC(O)O⁻, where R is an acyloxy substituent as defined below; e.g. AcO⁻), azide ($N_3^-$), thiocyanate (SCN⁻), nitro ($NO_2^-$), amine ($NH_2^-$). Those skilled in the art will be able to select suitable good leaving group in accordance with normal practice in organic chemistry.

Preferred examples of good leaving groups include methanesulphonate, 4-toluenesulphonate, trifluoromethylsulphonate, trifluoromethyltoluenesulphonate, imidizolsulphonate, or halide (i.e., F, Cl, Br, I).

Other substituents that may be present in the compounds disclosed herein include the following.

$C_{1-7}$alkyl: The term "$C_{1-7}$alkyl", as used herein, pertains to a monovalent moiety obtained by removing a hydrogen atom from a $C_{1-7}$ hydrocarbon compound having from 1 to 7 carbon atoms, which may be aliphatic or alicyclic, or a combination thereof, and which may be saturated, partially unsaturated, or fully unsaturated.

Examples of saturated linear $C_{1-7}$alkyl groups include, but are not limited to, methyl, ethyl, n-propyl, n-butyl, and n-pentyl (amyl). Examples of saturated branched $C_{1-7}$alkyl groups include, but are not limited to, iso-propyl, iso-butyl, sec-butyl, tert-butyl, and neo-pentyl.

Examples of saturated alicyclic $C_{1-7}$ alkyl groups (also referred to as "$C_{3-7}$ cycloalkyl" groups) include, but are not limited to, groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of unsaturated $C_{1-7}$ alkyl groups which have one or more carbon-carbon double bonds (also referred to as "$C_{2-7}$alkenyl" groups) include, but are not limited to, ethenyl (vinyl, —CH=CH₂), 2-propenyl (allyl, —CH—CH=CH₂), isopropenyl (—C(CH₃)=CH₂), butenyl, pentenyl, and hexenyl.

Examples of unsaturated $C_{1-7}$ alkyl groups which have one or more carbon-carbon triple bonds (also referred to as "$C_{2-7}$ alkynyl" groups) include, but are not limited to, ethynyl (ethinyl) and 2-propynyl (propargyl).

Examples of unsaturated alicyclic (carbocyclic) $C_{1-7}$ alkyl groups which have one or more carbon-carbon double bonds (also referred to as "$C_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-10}$ heterocyclyl: The term "$C_{3-10}$ heterocyclyl", as used herein, pertains to a monovalent moiety obtained by removing a hydrogen atom from a ring atom of a $C_{3-10}$ heterocyclic compound, said compound having one ring, or two or more rings (e.g., spiro, fused, bridged), and having from 3 to 10 ring atoms, atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. Ring heteroatoms may preferably be selected from the group consisting of O, N, S and P. "$C_{3-10}$" denotes ring atoms, whether carbon atoms or heteroatoms. Similarly, the term "$C_{3-10}$ heterocyclyl" will be understood to pertain to an equivalent moiety of 3 to 10 ring atoms, and so on.

$C_{5-20}$ aryl: The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms. The ring atoms may be all carbon atoms, as in "carboaryl groups", in which case the group may conveniently be referred to as a "$C_{5-20}$ carboaryl" group.

The above alkyl, heterocyclyl and aryl groups, whether alone or part of another substituent, may themselves optionally be substituted with one or more groups selected from themselves and the additional substituents listed and defined below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.

$C_{1-7}$ alkoxy: —OR, wherein R is a $C_{1-7}$ alkyl group. Examples of $C_{1-7}$ alkoxy groups include, but are not limited to, —OCH₃ (methoxy), —OCH₂CH₃ (ethoxy) and —OC(CH₃)₃ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam (2-pyrrolidone), δ-valerolactam, and ε-caprolactam.

Imino (imine): =NR, wherein R is an imino substituent, for example, hydrogen, $C_{1-7}$ alkyl group, a $C_{3-20}$heterocyclyl group, or a $C_{5-20}$ aryl group, preferably hydrogen or a $C_{1-7}$alkyl group.

Examples of imino groups include, but are not limited to, =NH, =NMe, =Net, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH₃ (acetyl), —C(=O)CH₂CH₃ (propionyl), —C(=O)C(CH₃)₃ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$alkyl group. Examples of ester groups include, but are not limited to, —C(=O)OCH₃, —C(=O)OCH₂CH₃, —C(=O)OC(CH₃)₃, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O) Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amino groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl and phthalimidyl.

Acylureido: —N(R$^1$)C(O)NR$^2$C(O)R$^3$ wherein R$^1$ and R$^2$ are independently ureido substituents, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. R$^3$ is an acyl group as defined for acyl groups. Examples of acylureido groups include, but are not limited to, —NHCONHC(O)H, —NHCONMeC(O)H, —NHCONEtC(O)H, —NHCONMeC(O)Me, —NHCONEtC(O)Et, —NMeCONHC(O)Et, —NMeCONHC(O)Me, —NMeCONHC(O)Et, —NMeCONMeC(O)Me, —NMeCONEtC(O)Et, and —NMeCONHC(O)Ph.

Carbamate: —NR$^1$—C(O)—OR$^2$ wherein R$^1$ is an amino substituent as defined for amino groups and R$^2$ is an ester group as defined for ester groups. Examples of carbamate groups include, but are not limited to, —NH—C(O)—O-Me, —NMe-C(O)—O-Me, —NH—C(O)—O-Et, —NMe-C(O)—O-t-butyl, and —NH—C(O)—O-Ph.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Tetrazolyl: a five membered aromatic ring having four nitrogen atoms and one carbon atom,

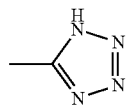

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amidine: —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. An example of an amidine group is —C(=NH)NH$_2$.

Carbazoyl (hydrazinocarbonyl): —C(O)—NN—R$^1$ wherein R$^1$ is an amino substituent as defined for amino groups. Examples of azino groups include, but are not limited to, —C(O)—NN—H, —C(O)—NN-Me, —C(O)—NN-Et, —C(O)—NN-Ph, and —C(O)—NN—CH$_2$-Ph.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Thio (sulfhydryl, thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$, —S(=O)$_2$C$_4$F$_9$ (nonaflyl), —S(=O)$_2$CH$_2$CF$_3$ (tresyl), —S(=O)$_2$Ph (phenylsulfonyl), 4-methylphenylsulfonyl (tosyl), 4-bromophenylsulfonyl (brosyl), and 4-nitrophenyl (nosyl).

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group.

Examples of sulfine groups include, but are not limited to, —S(=O)CH$_3$ and —S(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ and —OS(=O)$_2$CH$_2$CH$_3$.

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfinamino: —NR$^1$S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$.

Phosphoramidite: —OP(OR$^1$)—NR$^2{}_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_2$)—N(i-Pr)$_2$, and —OP(OCH$_2$CH$_2$CN)—N(i-Pr)$_2$.

Phosphoramidate: —OP(=O) (OR$^1$)—NR$^2{}_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_2$)—N(i-Pr)$_2$, and —OP(=O)(OCH$_2$CH$_2$CN)—N(i-Pr)$_2$.

In many cases, substituents may themselves be substituted. For example, a C$_{1-7}$ alkoxy group may be substituted with, for example, a C$_{1-7}$ alkyl (also referred to as a C$_{1-7}$ alkyl-C$_{1-7}$alkoxy group), for example, cyclohexylmethoxy, a C$_{3-20}$ heterocyclyl group (also referred to as a C$_{5-20}$ aryl-C$_{1-7}$ alkoxy group), for example phthalimidoethoxy, or a C$_{5-20}$ aryl group (also referred to as a C$_{5-20}$aryl-C$_{1-7}$alkoxy group), for example, benzyloxy.

C$_{1-12}$ Alkylene: The term "C$_{1-12}$ alkylene", as used herein, pertains to a bidentate moiety obtained by removing two hydrogen atoms, either both from the same carbon atom, or one from each of two different carbon atoms, of an aliphatic linear hydrocarbon compound having from 1 to 12 carbon atoms (unless otherwise specified), which may be saturated, partially unsaturated, or fully unsaturated. Thus, the term "alkylene" includes the sub-classes alkenylene, alkynylene, etc., discussed below.

Examples of saturated C$_{1-12}$ alkylene groups include, but are not limited to, —(CH$_2$)$_n$— where n is an integer from 1 to 12, for example, —CH$_2$— (methylene), —CH$_2$CH$_2$— (ethylene), —CH$_2$CH$_2$CH$_2$— (propylene), —CH$_2$CH$_2$CH$_2$CH$_2$— (butylene), and —CH$_2$CH$_2$CH$_2$CH$_2$CH$_2$— (pentylene).

Examples of partially unsaturated C$_{1-12}$ alkylene groups include, but is not limited to, —CH=CH— (vinylene), —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH— and —CH=CH—CH=CH—CH$_2$—.

Alkylene groups may optionally be substituted with one or more substituents including but not limited to those listed above. The C$_{1-12}$ alkylene chain may be interrupted with one or more divalent heteroatom groups such as, for example oxygen, nitrogen (which may be substituted with e.g. C$_{1-7}$ alkyl), or sulfur.

Where a particular label or definition (e.g. R) is applied to more than one substituent in one or more compounds, each incidence of that substituent is independent of the others, and may be the same as or different to any other substituent with that label.

Includes Other Forms:

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs:

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures or to a general formula includes structurally isomeric forms falling within that class or formula (e.g., C$_{1-7}$ alkyl includes n-propyl and iso-propyl; butyl includes n-, iso-, sec-, and tert-butyl; methoxyphenyl includes ortho-, meta-, and para-methoxyphenyl) and, except where specifically stated or indicated, all possible conformations and configurations of the compound(s) herein are intended to be included in the general formula (e).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

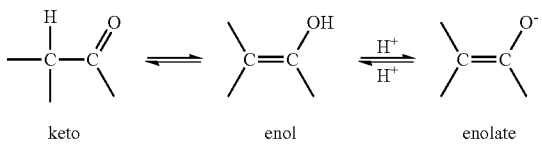

keto        enol        enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g., —COOH may be —COO$^-$, then a salt may be formed with a suitable cation. Examples of suitable inorganic cations include, but are not limited to, alkali metal ions such as Na$^-$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, 'Protective Groups in Organic Synthesis' (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_2$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO$).

For example, a carboxylic acid group may be protected as an ester for example, as: an C$_{1-7}$ alkyl ester (e.g. a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is C$_{1-7}$ alkyl (e.g. -Me, -Et); C$_{1-7}$ aminoalkyl (e.g. aminoethyl; 2-(N,N-diethylamino)ethyl; 2-(4-morpholino)ethyl); and acyloxy-C$_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxycarbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl) carbonyloxymethyl; and 1-(4-tetrahydropyranyl) carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Production of Glycosyl Transferases

In order to optimise the transfer of activated fluoro sialic acid compounds it may be desirable to identify and/or optimise the properties of a glycosyl transferase for use in accordance with the methods disclosed herein. The examples herein show that an α-2,3-(O)-sialyl transferase from S. frugiperda can be used to form conjugates between a sugar acceptor and the fluoro sialic acid compounds of the present invention. However, to improve the efficiency of this reaction, candidate enzymes may be developed, for example to improve one or more properties of the enzymes such as improved binding constant ($K_m$) and rate of catalytic turnover ($k_{cat}$) and/or substrate specificity. The development of glycosyl transferases may involve the use of techniques such as directed evolution as exemplified in Aharoni et al, Nature Methods, 2003, 3, 609-614.

Glycosylation

The ability to control glycosylation at defined sites using the present invention represents a useful tool for engineering glycosylation structures. This can be done by making the sugar acceptor part of a glycosylation structure that then reacts with the activated fluoro sialic acid compound. The glycosylation structure is generally a saccharide and may comprise a monoantennary structure, a biantennary structure, a triantennary structure or a complex glycosylation structure. The chemistry disclosed here may employ naturally occurring or synthetic monosaccharides, oligosaccharides or polysaccharides, and may be used to modify N-linked or O-linked glycosylation structures.

The methods of the present invention may include one or more further steps carried out as part of the synthesis of the glycosylation structures or their introduction into a therapeutic moiety such as a therapeutic polypeptide. These steps may be carried out on the therapeutic moiety comprising the glycosylation structure or on a glycosylation structure prior to its linkage to the therapeutic moiety. These steps include removing a terminal glycosyl group from a glycosylation structure to form the sugar acceptor group, for example in an enzymatic reaction using a sialidase. In embodiments in which the glycosylation structure is not linked to therapeutic moiety when the conjugation reaction is carried out, the methods may include the additional step of linking the conjugate to the therapeutic moiety. The methods may also include an initial step of introducing a glycosylation structure into a site in a polypeptide.

Alternatively or additionally, the methods of the present invention may be used for transferring a plurality of 3-fluoro sialic acid compounds to sugar acceptor. This may be done by transferring an oligomer comprising a plurality of 3-fluoro sialic acid compounds or by repeating the conjugation reaction.

Alternatively or additionally, the glycosylation structure may comprise linker group and/or other moieties such as one or more poly(alkylene glycol) molecules. In one preferred example, the polypeptide is represented by the schematic formula:

$$\text{Polypeptide-AA-L}^1\text{-Gly}$$

wherein:

AA is a terminal or internal amino acid residue of the polypeptide;

$L^1$ is an optional linker group covalently linked to the amino acid AA;

Gly represents the sugar acceptor group which is optionally part of a glycosylation structure.

In many cases, the therapeutic moiety will be a polypeptide, although the present invention is generally applicable to any type of therapeutic moiety in that includes glycosylation or in which it is desired to introduce glycosylation. Polypeptides include therapeutic proteins and antibodies, and fragments thereof, for example to control their immunogenicity and pharmacological properties such as half-life. At present, the manufacture of recombinant protein therapeutics is expensive and slow as mammalian cell lines are often used for manufacture to ensure that the proteins are glycosylated. The methods disclosed herein may be used to add glycosylation to a polypeptide after production in bacterial cell lines, in which expression is generally more efficient, thereby helping to improve the speed and/or economy of protein production, while retaining the glycosylation. Alternatively, for polypeptides expressed in cell lines that glycosylate expression products, the present invention may be used as modify or add glycosylation.

In preferred embodiments, the carbohydrates employed may comprise chemically modified derivatives of naturally occurring branched oligosaccharides commonly displayed on N- or O-linked glycoproteins, or degradation products thereof. Carbohydrate groups that may be used in the present invention are well known in the art and include carbohydrate groups found in the N- and O-linked glycosylation of eukaryotic proteins and man made carbohydrate groups, e.g. see the carbohydrate groups and methods of producing and identifying them disclosed in WO 2003/025133 and WO 2004/083807.

N-Linked glycans are found attached to the R-group nitrogen (N) of asparagine in the sequon. The sequon is a Asn-X-Ser or Asn-X-Thr sequence, where X is any amino acid except proline and may be composed of N-acetyl galactosamine, galactose, neuraminic acid, N-acetylglucosamine, fructose, mannose, fucose and other monosaccharides.

In eukaryotes, N-linked glycans are derived from a core 14-sugar unit assembled in the cytoplasm and endoplasmic reticulum. First, two N-acetyl glucosamine residues are attached to dolichol phosphate, a lipid, on the external side of the endoplasmic reticulum membrane. Five mannose residues are then added to this structure. At this point, the partially finished core glycan is flipped across the endoplasmic reticulum membrane, so that it is now located within the reticular lumen. Assembly then continues within the endoplasmic reticulum, with the addition of four more mannose residues. Finally, three glucose residues are added to this structure. Following full assembly, the glycan is transferred en bloc by the glycosyltransferase oligosaccharyltransferase to a nascent peptide chain, within the reticular lumen. This core structure of N-linked glycans thus consists of 14 residues (3 glucose, 9 mannose, and 2 N-acetylglucosamine).

In eukaryotes, O-linked glycans, are assembled one sugar at a time on a serine or threonine residue of a peptide chain in the Golgi apparatus. Unlike with N-linked glycans, there is as of yet no known consensus sequence. However, the placement of a proline residue at either −1 or +3 relative to the serine or threonine is favourable for O-linked glycosylation.

The first monosaccharide attached in the synthesis of O-linked glycans is N-acetyl-galactosamine. After this, several different pathways are possible. A Core 1 structure is generated by the addition of galactose. A Core 2 structure is generated by the addition of N-acetyl-glucosamine to the N-acetyl-galactosamine of the Core 1 structure. Core 3 structures are generated by the addition of a single N-acetyl-glucosamine to the original N-acetyl-galactosamine. Core 4 structures are generated by the addition of a second N-acetyl-glucosamine to the Core 3 structure. Other core structures are possible, though are less common. A common structural theme in O-linked glycans is the addition of polylactosamine units to the various core structures. These are formed by the repetitive addition of galactose and N-acetyl-glucosamine units. Polylactosamine chains on O-linked glycans are often capped by the addition of a sialic acid residue (similar to neuraminic acid). If a fucose residue is also added, to the next to penultimate residue, a sialyl-lewis-X (SLex)) structure is formed.

Examples of glycosylation structure include the following O-linked and N-linked structures:

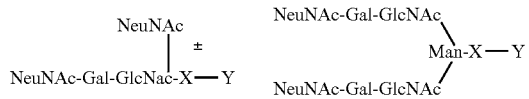

wherein X is a linker as discussed herein and Y is hydrogen or a protein or polypeptide.

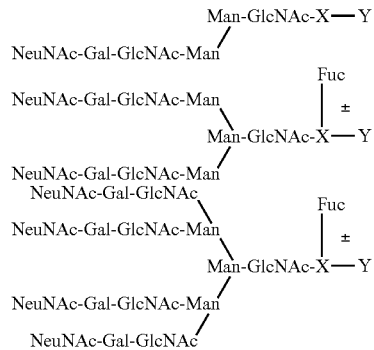

wherein X is a glycan group or a linker as discussed herein and Y is hydrogen or a protein or polypeptide.

Polypeptides

The methods of the present invention are generally applicable to a range of applications based on the reaction being capable of modifying the glycosylation, and in particular adding sialic acid groups, to therapeutic moieties such as polypeptides. Polypeptides as used herein includes polymers in which the monomers are amino acids and are joined together through amide bonds. The amino acids forming polypeptides may include unnatural amino acids, such as β-alanine, phenylglycine and homoarginine, or amino acids that are not nucleic acid-encoded, and/or amino acids that have been modified to include reactive groups, glycosylation sites, polymers, therapeutic moieties, biomolecules and the like may also be used in the invention. All of the amino acids used in the present invention may be either the D- or L forms. The use of the naturally occurring L-isomer is generally preferred. The polypeptides that may be used in the present invention may initially be glycosylated or unglycosylated polypeptides, and this includes polypeptides that are incompletely glycosylated by a system that expresses them.

The methods described are applicable to any size or type of polypeptide from single amino acids and peptides to polypeptides and proteins having molecular weights of up to or over 100 kDa. Accordingly, while for convenience, the methods herein are generally described by reference to "polypeptides", this should be taken to include shorter sequences of amino acids (e.g., from 2, 3, 4, 5 or 10 amino acids in length to 30, 40 or 50 amino acids in length), sometimes referred to in the art as peptides. The term should also be taken to include polypeptides having secondary, tertiary or quaternary structure generally referred to as proteins, as well as multidomain proteins.

The methods and reagents disclosed herein are particularly useful for functionalising therapeutic polypeptides, for example to modify their pharmacological properties such as stability, biological half-life or water solubility, or the immunologic characteristics of the polypeptide.

Example of suitable classes of polypeptides that may be modified in accordance with the present invention include erythropoietins (EPO), interferons, interleukins, chemokines, lymphokines, cytokines, insulin, monoclonal antibodies and fragments, recombinant antibodies and fragments, blood-clotting factors, colony-stimulating factors (CSFs), growth hormones, plasminogen activators, virally-derived peptides, reproductive hormones and therapeutic enzymes. Specific examples of polypeptides that may be employed include colony stimulating factor (CSF), granulocyte colony stimulating factor (G-CSF), granulocyte macrophage colony stimulating factor (GM-CSF), Factor VIIa, Factor VIII, Factor IX, human growth hormone (hGH), DNase, insulin, glucagon, VEGF, VEGF receptor, TNF, TNF receptor, platelet-derived growth factor (PDGF), tissue plasminogen activator (tPA), erythropoietin (EPO), enfurvirtide, insulin-like growth factor (IGF), nerve growth factor (NGF), IL-1, IL-2, IL-6, IL-10, IL-12, IL-18, IL-24, interferon beta-1a, interferon beta-1b, interferon alpha-2a, interferon alpha-2b, interferon alpha, or interferon gamma.

In the present invention, references to polypeptides that are antibodies includes immunoglobulins whether natural or partly or wholly synthetically produced. The term also covers any polypeptide or protein comprising an antigen binding domain. Antibody fragments which comprise an antigen binding domains include Fab, scFv, Fv, dAb, Fd fragments, diabodies, triabodies or nanobodies. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2,188,638 A or EP 0 239 400 A. Antibodies can be modified in a number of ways and the term should be construed as covering any specific binding member or substance having an antibody antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP 0 120 694 A and EP 0 125 023 A.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242; 423-426, 1988; Huston et al, PNAS USA, 85: 5879-5883, 1988); (viii) bispecific single chain Fv dimers (PCT/US92/09965) and (ix) "diabodies", multivalent or multispecific fragments constructed by gene fusion (WO 94/13804; Holliger et al, P.N.A.S. USA, 90: 6444-6448, 1993). Fv, scFv or diabody molecules may be stabilised by the incorporation of disulphide bridges linking the VH and VL domains (Reiter et al, Nature Biotech, 14: 1239-1245, 1996). Minibodies comprising a scFv joined to a CH3 domain may also be made (Hu et al, Cancer Res., 56: 3055-3061, 1996).

Pegylation

Alternatively or in addition to the present invention being employed to modify the glycosylation of polypeptides, the methods disclosed herein may be used as part of a procedure to pegylate a given polypeptide. Pegylation is one approach that can also be employed to engineer therapeutic proteins so that they contain other moieties useful for modifying their pharmacological properties. One preferred example is the conjugation of polypeptides to poly(alkylene glycol) molecules, in particular polyethylene glycol (PEG) molecules, that may be used to enhance the half life or other pharmacological properties of polypeptide therapeutics. The present methods provide the opportunity to pegylate proteins of interest in a selective way depending on where the thiol groups are present in the protein. Poly(alkylene glycol) molecules are interchangeably referred to in the art as poly(alkylene oxide) molecules and are polyethers. Poly(alkylene glycol) molecules may have linear, branched, comb or star structures and generally are highly water soluble.

In accordance with the present invention, the glycosylation structure may comprise or be linked to one or more poly(alkylene) glycol groups. These groups may be serve as a linker between the therapeutic moiety and the glycosylation structure.

In addition, the basic poly(alkylene glycol) structure may be provided with one or more reactive functional groups such as hydroxy, amine, carboxylic acid, alkyl halide or thiol groups to facilitate the reaction of the poly(alkylene glycol) molecule with other species such as polypeptides. Preferred poly(alkylene glycol) molecules include those substituted at one or more hydroxyl positions with a chemical group, such as an alkyl group having between one and four carbon atoms. The most preferred poly(alkylene glycol) molecules for use in accordance with the present invention are polyethylene glycol ("PEG") molecules, although the skilled person would be able to use the techniques disclosed herein in conjunction with other poly(alkylene glycol) molecules, such as polypropylene glycol or polyethylene-polypropylene glycol copolymers. Poly(alkylene glycol) molecules, including PEGs, typically have molecular weights between about 400 Da and about 80 kDa, more preferably between about 1 kDa and about 60 kDa, and more preferably between about 5 kDa and about 50 kDa, e.g. molecular weights of 10 kDa, 20 kDa, 30 kDa or 40 kDa. Poly(alkylene glycol) molecules that may be used in accordance with the present invention are well known in the art and publicly available, for example from commercially available sources such as SigmaAldrich.

Pegylation is a known strategy for modifying the properties of therapeutic polypeptides, such as peptides, proteins and antibodies. In general, the attachment of PEG molecules to polypeptides is used to alter their conformation, electrostatic or hydrophobic properties, and lead to improvements in their biological and pharmacological properties, such as increasing drug solubility, reducing dosage frequency, modulating (especially increasing) circulating half-life, increasing drug stability and increasing resistance to proteolytic degradation Pegylation works by increasing the molecular weight of the therapeutic polypeptide by conjugating the polypeptide to one or more PEG polymer molecules. The methods of the present invention have the advantage that the site of introduction of the PEG molecules into a polypeptide is defined by the presence of thiol groups.

Linkers and their Use

In some embodiments of the present invention, the glycosylation of the polypeptide may be linked to a terminal or internal amino acid residue of the polypeptide via a linker group. In one preferred aspect of the present invention, this linker group may comprise a nitrogen containing heterocyclic aromatic ring having a vinyl substituent for reaction with one or more thiol groups that are naturally present, or have been introduced into, the polypeptide, e.g. a thiol group of one or more cysteine residues. These linker groups have positions which may additionally be linked to a coupling partner that is capable of altering properties of the polypeptide such as a poly(alkylene glycol) molecule or a glycan group. Examples of this type of linker and the methods for coupling them to amino acids in polypeptides where it is desired to introduce glycosylation are described in GB-A-0823309.0, which is hereby expressly incorporated by reference in its entirety.

EXAMPLES

The following examples are set forth so as to provide those of ordinary skill in the art with a complete disclosure and description of how to practice the invention, and are not intended to limit the scope of the invention.

Experimental

Synthesis of an Activated 3-Fluorosialic Acid Donor

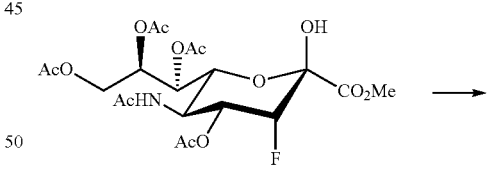

Chemical Formula: $C_{20}H_{28}FNO_{13}$
Exact Mass: 509.1545
Molecular Weight: 509.4336

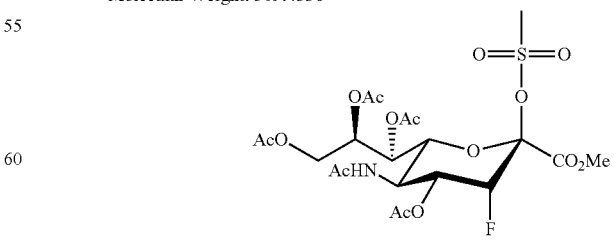

Chemical Formula: $C_{21}H_{30}FNO_{15}S$
Exact Mass: 587.1320
Molecular Weight: 587.5240

The hemiacetal (173 mg) was dissolved in 5 ml of $CH_2Cl_2$ and kept under $N_2$ gas. To the solution was added pyridine (164.8 μl, 6 eq.) and mesyl chloride (79.2 μl, 3 eq.). The reaction was left to stir at R.T. for 5 hours. The reaction was concentrated and purified by silica gel chromatography (10% EtOAc/petroleum ether→10% MeOH/EtOAc) to yield a white product (152 mg, 76% yield). $^1$H NMR, 400 MHz (CDCl$_3$): 5.66 (br. s, 1H), 5.47 (dd, 1H, J=1.6 and 4.7 Hz), 5.40-5.21 (m, 2H), 4.92 (dd, 1H, H-3, J=2.3, 48.9 Hz), 4.66 (dd, 1H, J=2.3 and 12.5 Hz), 4.49-4.43 (m, 2H), 4.17 (dd, 1H, J=6.7 and 12.5 Hz), 3.91 (s, 3H), 3.18 (s, 3H), 2.15 (s, 3H), 2.10 (s, 3H), 2.07 (s, 3H), 2.02 (s, 3H), 1.90 (s, 3H). $^{19}$F NMR, 400 MHz (CDCl$_3$): −206.00 (dd, J=28.8 and 48.9 Hz). ESI-MS: Expected for molecular ion $C_{21}H_{30}FN_2O_{15}S$=587.1320. Found M+Na$^+$=610.1235.

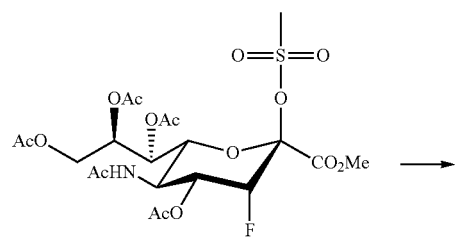

Chemical Formula: $C_{21}H_{30}FNO_{15}S$
Exact Mass: 587.1320
Molecular Weight: 587.5240

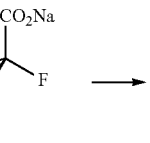

Chemical Formula: $C_{12}H_{20}FNO_{11}S$
Exact Mass: 405.0741
Molecular Weight: 405.3507

The fully protected mesyl sialic acid (72 mg, 0.123 mmol) was dissolved in THF (4 ml). To this was added 1M NaOH (7.5 eq., 0.92 ml). The reaction was sonicated for 30 s and left to stir at 4° C. overnight. The reaction was neutralised with amberlite IR 120$^+$, filtered and the volume reduced in vacuo. The remaining solution was freeze-dried to yield the deprotected mesylate as a white powder (30 mg), which was used without further purification. ESI-MS: Expected for molecular ion $C_{12}H_{20}FNO_{11}S$=405.0741. Found M-H$^+$=404.0683.

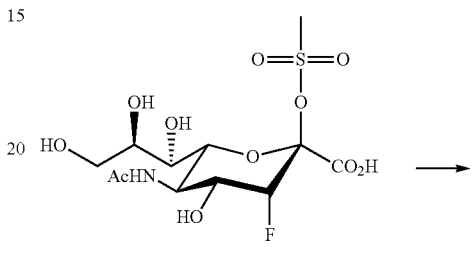

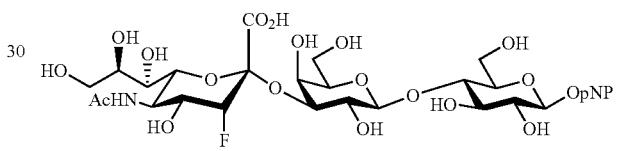

Chemical Formula: $C_{29}H_{41}FN_2O_{21}$
Exact Mass: 772.2186
Molecular Weight: 772.6350

The mesyl-sialic acid (3 mg, 7.4 μmol) was added to a solution containing 1 mM manganese chloride, 10 mM pNP-lactose, 50 mM sodium citrate buffer [pH=6.0, with 5% (v/v) Triton-X and 0.5% (w/v) bovine serum albumin], 5 mM cytosine, 5 mM cytidine and 20 μL α-2,3-(O)-sialyl transferase (rat recombinant, *S. frugiperda*, 0.8 mg/ml). The reaction was incubated at 37° C. for 18 hours then analysed by mass spectrometry. Expected for molecular ion $C_{29}H_{41}F_1N_2O_{21}$=772.2186. Found M-H$^+$=771.2123.

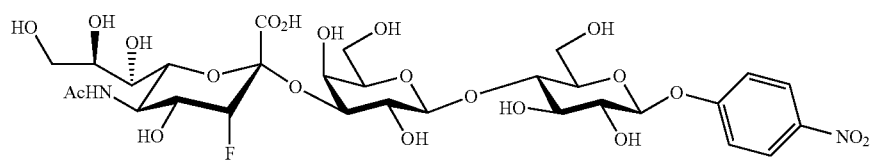

The difluoro-sialic acid (3 mg, 9.1 μmol) was added to a solution containing 10 mM pNP-lactose, 30 mM sodium chloride, 20 mM Tris-HCl buffer [pH=7.6] and 40 μL *T. cruzi* trans-sialidase (1.0 mg/ml). The reaction was incubated at 37° C. for 18 hours then analysed by mass spectrometry confirming the production of the 3-fluorosialyl lactose product. Expected for molecular ion $C_{29}H_{41}F_1N_2O_{21}$=772.2186. Found M-H+=771.2117.

While the foregoing invention has been described in some detail for purposes of clarity and understanding, it will be clear to one skilled in the art from a reading of this disclosure that various changes in form and detail may be made. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

REFERENCES

U.S. Pat. No. 7,226,903
Chiu et al., Nat. Struct. Mol. Biol. (2004) 11, 163-170
Watts et al., J. Am. Chem. Soc. (2003) 125, 7532-7533
Watts et al., Can. J. Chem. (2004) 82, 1581-1588
Watts et al., J. Biol. Chem. (2006) 281, 4149-4155
Harshal et al., J. Am. Chem. Soc. (2007) 129, 10630-10631
Aharoni et al., Nature Methods, 2003, 3, 609-614
Sun et al., Eur. J. Org. Chem. (2000), 2643-2653

The invention claimed is:

1. A method for glycosylating a therapeutic polypeptide, by forming a covalent conjugate between a 3-fluorosialic acid compound and a sugar acceptor covalently linked to the therapeutic polypeptide, said sugar acceptor including a terminal glycosyl residue, the method comprising contacting the sugar acceptor and 3-fluorosialic acid compound, the contacting step taking place under conditions suitable for reacting and covalently bonding the 3-fluorosialic acid compound to the sugar acceptor and yielding a glycosylation structure wherein said 3-fluorosialic compound is a terminal glycosyl group of said glycosylation structure, wherein the 3-fluorosialic acid compound does not comprise a cytosine monophosphate (CMP) group, and wherein the 3-fluorosialic acid compound is represented by general formula (I):

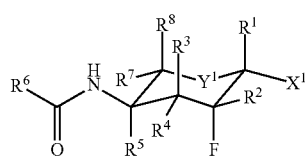

(I)

wherein:
$Y^1$ is selected from —O—, —S—, or —NR—, wherein R is independently selected from H, $C_{1-7}$ alkyl, $C_{3-10}$ heterocyclyl, or $C_{5-20}$ aryl;
$R^1$ is a leaving group effective to support and stabilize a negative charge, with the proviso that said leaving group is not a cytosine monophosphate (CMP) group;
$X^1$ is —$CO_2R$, wherein R is as defined above;
$R^2$ is selected from H, halide or OH;
$R^3$ and $R^4$ are each independently selected from H, —OR, —$NR_2$ or —$Z^1(CH_2)_mZ^2$, where R is as defined above, $Z^1$ is selected from —O—, —NR—, —$CR_2$— and —S—, m is from 0 to 5 and $Z^2$ is selected from —OR, —$NR_2$ or —CN; with the proviso that $R^3$ and $R^4$ cannot both be H;
$R^5$ is H;
$R^6$ is selected from $C_{1-7}$ alkyl; $C_{1-7}$ hydroxyalkyl, $C_{1-7}$ amino alkyl or $C_{1-7}$ thioalkyl;
$R^7$ is represented by the formula:

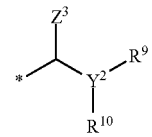

wherein $Y^2$ is selected from N, O, S, and CH; $Z^3$ is selected from H, hydroxyl, halide, $C_{1-7}$ alkyl, $C_{1-7}$ aminoalkyl, $C_{1-7}$ hydroxyalkyl, or $C_{1-7}$ thioalkyl; $R^9$ and $R^{10}$ are independently selected from H, hydroxyl, $C_{1-7}$ hydroxyalkyl, $C_{1-7}$ alkyl, $C_{5-20}$ aryl, $C(O)Z^4$, wherein $Z^4$ is selected from $C_{1-7}$ alkyl or $C_{5-20}$ aryl, with the proviso that if $Y^2$ is O or S, $R^{10}$ is absent;
or wherein $R^4$ is other than hydroxyl, $R^7$ may additionally be $C_{1-7}$ hydroxyalkyl;
$R^8$ is hydrogen;
or an oligomer of two or more molecules of formula (I);
or stereoisomeric forms, tautomeric forms, salts, solvates, or chemically protected forms thereof.

2. The method of claim 1, wherein the method comprises contacting the sugar acceptor, the 3-fluorosialic acid compound and an enzyme capable of transferring the 3-fluorosialic acid compound to the sugar acceptor, the contacting step taking place under conditions suitable for the transfer and covalent bonding of the 3-fluorosialic acid compound to the sugar acceptor.

3. The method of claim 1, wherein the 3-fluorosialic acid compound is covalently bonded to the sugar acceptor via a synthetic chemical reaction.

4. The method of claim 1, wherein $R^1$ is methanesulphonate, 4-toluenesulphonate, trifluoromethylsulphonate, trifluoromethyltoluenesulphonate, imidizolsulphonate, or a halide.

5. The method of claim 1, wherein the sugar acceptor is part of said glycosylation structure.

6. The method of claim 5, wherein the glycosylation structure comprises a naturally occurring or synthetic monosaccharide, oligosaccharide or polysaccharide.

7. The method of claim 5, wherein the glycosylation structure comprises a N-linked or O-linked saccharide group.

8. The method of claim 5, wherein, prior to glycosylation with 3-fluorosialic acid, the terminal glycosyl residue of the sugar acceptor is removed enzymatically using a sialidase.

9. The method of claim 2, wherein the method comprises transferring a plurality of 3-fluorosialic acid compounds to the sugar acceptor.

10. The method of claim 2, wherein the method comprises transferring a plurality of 3-fluorosialic acid groups to one or more terminal glycosyl residues of the glycosylation structure present on a polypeptide.

11. The method of claim 2, wherein the enzyme for transferring the 3-fluorosialic acid group is a sialyl transferase.

12. The method of claim 2, wherein the enzyme for transferring the 3-fluorosialic acid group is a trans-sialidase.

13. The method of claim 5, which comprises the initial step of introducing a sugar acceptor into a site in a polypeptide.

14. The method of claim 13, wherein the polypeptide is represented by the schematic formula:

Polypeptide-AA-L¹-Gly wherein:
AA is a terminal or internal amino acid residue of the polypeptide;
L¹ is an optional linker group covalently linked to the amino acid AA;
Gly represents the sugar acceptor group which is optionally part of a glycosylation structure.

15. The method of claim 13, wherein the polypeptide is an erythropoietin, an interferon, an interleukin, a chemokine, a lymphokine, a cytokine, insulin, a monoclonal antibody or fragment thereof, a recombinant antibody or fragment thereof, a blood-clotting factor, a colony-stimulating factor, a growth hormone, a plasminogen activator, a virally-derived peptide, a reproductive hormone or a therapeutic enzyme.

16. A conjugate produced by the method of claim 1.

17. A conjugate of a therapeutic polypeptide comprising a glycosylation structure, wherein the glycosylation structure comprises at least one 3-fluoro sialic acid compound, said 3-fluoro sialic acid compound(s) being at least one terminal glycosyl group of the glycosylation structure, wherein said glycosylation structure is covalently bonded to said at least one 3-fluoro sialic acid compound, wherein the 3-fluoro sialic acid compound does not comprise a cytidine monophosphate (CMP) group, and wherein the 3-fluoro sialic acid compound is represented by general formula (II):

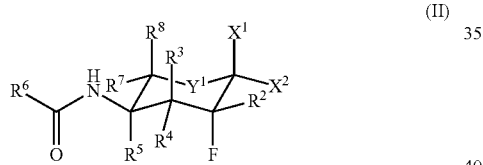

(II)

wherein:
$Y^1$ is selected from —O—, —S—, or —NR—, wherein R is independently selected from H, $C_{1-7}$ alkyl, $C_{3-10}$ heterocyclyl, or $C_{5-20}$ aryl;
$X^1$ is —$CO_2R$, wherein R is as defined above;
$X^2$ represents the remaining part of the glycosylation structure and comprises at least two saccharide units;
$R^2$ is selected from H, halide or OH;
$R^3$ and $R^4$ are each independently selected from H, —OR, —$NR_2$ or —$Z^1(CH_2)_mZ^2$, where R is as defined above, $Z^1$ is selected from —O—, —NR—, —$CR_2$— and —S—, m is from 0 to 5 and $Z^2$ is selected from —OR, —$NR_2$ or —CN; with the proviso that $R^3$ and $R^4$ cannot both be H;
$R^5$ is H;
$R^6$ is selected from $C_{1-7}$ alkyl; $C_{1-7}$ hydroxyalkyl, $C_{1-7}$ amino alkyl or $C_{1-7}$ thioalkyl;
$R^7$ is represented by the formula:

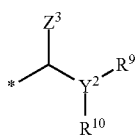

wherein $Y^2$ is selected from N, O, S, and CH; $Z^3$ is selected from H, hydroxyl, halide, $C_{1-7}$ alkyl, $C_{1-7}$ aminoalkyl, $C_{1-7}$ hydroxyalkyl, or $C_{1-7}$ thioalkyl; $R^9$ and $R^{10}$ are independently selected from H, hydroxyl, $C_{1-7}$ hydroxyalkyl, $C_{1-7}$ alkyl, $C_{5-20}$ aryl, $C(O)Z^4$, wherein $Z^4$ is selected from $C_{1-7}$ alkyl or $C_{5-20}$ aryl, with the proviso that if $Y^2$ is O or S, $R^{10}$ is absent;
or wherein $R^4$ is other than hydroxyl, $R^7$ may additionally be $C_{1-7}$ hydroxyalkyl;
$R^8$ is hydrogen;
or (ii) an oligomer of two or more molecules of formula (II), and wherein said at least two saccharide units of $X^2$ comprise at least one further 3-fluoro sialic acid group;
or stereoisomeric forms, tautomeric forms, salts, solvates, or chemically protected forms of (i) and (ii).

18. The conjugate of claim 17, wherein the glycosylation structure is linked to the polypeptide at a glycosylation site and/or via an amino acid residue of the polypeptide, optionally via a linker group.

19. A glycosylation structure comprising at least one 3-fluoro sialic compound, said 3-fluoro sialic acid compound(s) being at least one terminal glycosyl group of the glycosylation structure, wherein the structure is represented by (i) the formula (II):

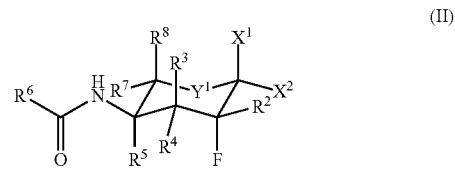

(II)

wherein:
$Y^1$ is selected from —O—, —S—, or —NR—, wherein R is independently selected from H, $C_{1-7}$ alkyl, $C_{3-10}$ heterocyclyl, or $C_{5-20}$ aryl;
$X^1$ is —$CO_2R$, wherein R is as defined above;
$X^2$ represents the remaining part of the glycosylation structure and comprises at least two saccharide units;
$R^2$ is selected from H, halide or OH;
$R^3$ and $R^4$ are each independently selected from H, —OR, —$NR_2$ or —$Z^1(CH_2)_mZ^2$, where R is as defined above, $Z^1$ is selected from —O—, —NR—, —$CR_2$— and —S—, m is from 0 to 5 and $Z^2$ is selected from —OR, —$NR_2$ or —CN; with the proviso that $R^3$ and $R^4$ cannot both be H;
$R^5$ is H;
$R^6$ is selected from $C_{1-7}$ alkyl; $C_{1-7}$ hydroxyalkyl, $C_{1-7}$ amino alkyl or $C_{1-7}$ thioalkyl;
$R^7$ is represented by the formula:

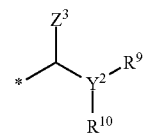

wherein $Y^2$ is selected from N, O, S, and CH; $Z^3$ is selected from H, hydroxyl, halide, $C_{1-7}$ alkyl, $C_{1-7}$ aminoalkyl, $C_{1-7}$ hydroxyalkyl, or $C_{1-7}$ thioalkyl; $R^9$ and $R^{10}$ are independently selected from H, hydroxyl, $C_{1-7}$ hydroxyalkyl, $C_{1-7}$ alkyl, $C_{5-20}$ aryl, $C(O)Z^4$, wherein $Z^4$ is selected from $C_{1-7}$ alkyl or $C_{5-20}$ aryl, with the proviso that if $Y^2$ is O or S, $R^{10}$ is absent;
or wherein $R^4$ is other than hydroxyl, $R^7$ may additionally be $C_{1-7}$ hydroxyalkyl;
$R^8$ is hydrogen;
or (ii) an oligomer of two or more molecules of formula (II), and wherein said at least two saccharide units of $X^2$ comprise at least one further 3-fluoro sialic acid group;
or stereoisomeric forms, tautomeric forms, salts, solvates, or chemically protected forms of (i) and (ii).

20. The glycosylation structure of claim 19, wherein the glycosylation structure comprises a monoantennary structure, a biantennary structure, a triantennary structure or a complex glycosylation structure.

21. The glycosylation structure of claim 19, wherein the glycosylation structure comprises a naturally occurring or synthetic monosaccharide, oligosaccharide or polysaccharide.

22. The glycosylation structure of claim 19, wherein the at least two saccharide units of the glycosylation structure are N-linked or O-linked.

23. A conjugate of a glycosylation structure of claim 19 and a therapeutic polypeptide, wherein the glycosylation structure is covalently bonded to one or more 3-fluoro sialic acid groups, wherein the 3-fluoro sialic acid groups form the terminal glycosyl group of the glycosylation structure.

24. A pharmaceutical composition comprising a conjugate according to claim 17 and a pharmaceutically acceptable carrier.

25. The method of claim 12, wherein the enzyme is a trans-sialidase that has been genetically engineered to improve at least one of rate of transfer reaction and binding of the donor 3-fluoro sialic acid molecule.

26. A glycosylated polypeptide, obtained by a method comprising covalently bonding at least one 3-fluoro sialic acid compound to a terminal group of a glycosylation structure comprising at least two saccharide units, the glycosylation structure being chemically linked to said polypeptide.

27. The glycosylated polypeptyide of claim 26, wherein the 3-fluoro sialic acid compound used in the method does not comprise a cytidine monophosphate (CMP) group.

28. The glycosylated polypeptide of claim 26, wherein said 3-fluoro sialic acid compound is covalently bonded to a naturally occurring glycosylation structure.

29. The glycosylated polypeptide of claim 26, wherein said 3-fluoro sialic acid compound is covalently bonded to a synthetic glycosylation structure.

30. The method of claim 26, wherein a plurality of 3-fluoro sialic acid compounds are covalently bonded to the glycosylation structure.

31. The glycosylated polypeptide of claim 26, wherein said polypeptide is a therapeutic polypeptide.

32. The glycosylated polypeptide of claim 31, wherein said therapeutic polypeptide is selected from the group consisting of erythropoietin, an interferon, an interleukin, a chemokine, a lymphokine, a cytokine, insulin, a monoclonal antibody or fragment thereof, a recombinant antibody or fragment thereof, a blood-clotting factor, a colony-stimulating factor, a growth hormone, a plasminogen activator, a virally-derived peptide, a reproductive hormone or a therapeutic enzyme.

33. The glycosylated polypeptide of claim 26, wherein the at least one 3-fluoro sialic acid is covalently bonded to the glycosylation structure in the presence of an enzyme selected from the group consisting of a sialyl transferase and a trans-sialidase.

34. The glycosylated polypeptide of claim 26, wherein the polypeptide is represented by the schematic formula:
Polypeptide-AA-$L^1$-Gly
wherein:
AA is a terminal or internal amino acid residue of the polypeptide;
$L^1$ is an optional linker group covalently linked to the amino acid AA;
Gly represents the sugar acceptor group which is optionally part of a glycosylation structure.

35. The glycosylated polypeptide of claim 26, wherein the glycosylation structure comprises a naturally occurring or synthetic monosaccharide, oligosaccharide or polysaccharide.

36. The glycosylated polypeptide of claim 26, wherein the at least two saccharide units of the glycosylation structure are N-linked or O-linked.

37. The glycosylation structure of claim 19 which comprises at least one 3-fluoro sialic acid group and two further saccharide units.

38. A method for glycosylating a therapeutic polypeptide, by forming a covalent conjugate between a 3-fluorosialic acid compound and sugar acceptor covalently linked to the therapeutic polypeptide, said sugar acceptor including a terminal glycosyl residue, the method comprising:
(a) contacting the sugar acceptor and 3-fluorosialic acid compound, the contacting step taking place under conditions suitable for reacting and covalently bonding the 3-fluorosialic acid compound to the sugar acceptor and yielding a glycosylation structure wherein said 3-fluoro sialic compound is a terminal glycosyl group of said glycosylation structure, wherein the 3-fluoro ialic acid compound does not comprise a cytosine monophosphate (CMP) group, and wherein the sugar acceptor is present on the polypeptide, wherein the 3-fluorosialic acid compound is represented by general formula (I):

$$\text{(I)}$$

wherein:
$Y^1$ is selected from —O—, —S—, or —NR—, wherein R is independently selected from H, $C_{1-7}$ alkyl, $C_{3-10}$ heterocyclyl, or $C_{5-20}$ aryl;
$R^1$ is a leaving group effective to support and stabilize a negative charge, with the proviso that said leaving group is not a cytosine monophosphate (CMP) group;
$X^1$ is —$CO_2R$, wherein R is as defined above;
$R^2$ is selected from H, halide or OH;
$R^3$ and $R^4$ are each independently selected from H, —OR, —$NR_2$ or —$Z^1(CH_2)_mZ^2$, where R is as defined above, $Z^1$ is selected from —O—, —NR—, —$CR_2$— and —S—, m is from 0 to 5 and $Z^2$ is selected from —OR, —$NR_2$ or —CN; with the proviso that $R^3$ and $R^4$ cannot both be H;
$R^5$ is H;
$R^6$ is selected from $C_{1-7}$ alkyl; $C_{1-7}$ hydroxyalkyl, $C_{1-7}$ amino alkyl or $C_{1-7}$ thioalkyl;

$R^7$ is represented by the formula:

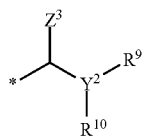

wherein $Y^2$ is selected from N, O, S, and CH; $Z^3$ is selected from H, hydroxyl, halide, $C_{1-7}$ alkyl, $C_{1-7}$ aminoalkyl, $C_{1-7}$ hydroxyalkyl, or $C_{1-7}$ thioalkyl; $R^9$ and $R^{10}$ are independently selected from H, hydroxyl, $C_{1-7}$ hydroxyalkyl, $C_{1-7}$ alkyl, $C_{5-20}$ aryl, $C(O)Z^4$, wherein $Z^4$ is selected from $C_{1-7}$ alkyl or $C_{5-20}$ aryl, with the proviso that if $Y^2$ is O or S, $R^{10}$ is absent;

or wherein $R^4$ is other than hydroxyl, $R^7$ may additionally be $C_{1-7}$ hydroxyalkyl;

$R^8$ is hydrogen;

or an oligomer of two or more molecules of formula (I);

or stereoisomeric forms, tautomeric forms, salts, solvates, or chemically protected forms thereof; and (b) covalently linking said glycosylation structure to a polypeptide.

* * * * *